United States Patent [19]

Steele et al.

[11] Patent Number: 5,010,009
[45] Date of Patent: Apr. 23, 1991

[54] MATERIAL FOR CELL ATTACHMENT AND GROWTH

[75] Inventors: John Steele, North Rocks; Oddvar Johansen, Mulgrave; Graham Johnson, Peakhurst; Johnathon Hodgkin, Burwood, all of Australia

[73] Assignee: Commonwealth Scientific & Industrial Research Organisation & Telectronics Pty. Limited, Australia

[21] Appl. No.: 477,884

[22] PCT Filed: Aug. 22, 1989

[86] PCT No.: PCT/AU89/00356
§ 371 Date: May 9, 1990
§ 102(e) Date: May 9, 1990

[87] PCT Pub. No.: WO90/02145
PCT Pub. Date: Mar. 8, 1990

[30] Foreign Application Priority Data

Aug. 22, 1988 [AU] Australia ................. PJ0020

[51] Int. Cl.$^5$ ............ C12N 5/02; A61K 47/00
[52] U.S. Cl. ............ 435/240.243; 435/180; 427/2; 427/36; 427/53.1; 427/337; 427/385.5; 525/276; 623/1; 623/12; 623/15

[58] Field of Search ............ 427/2, 36, 53.1, 337, 427/384, 385.5; 623/1, 12, 15; 435/180, 181, 240.23, 240.24, 240.243, 240.25; 525/54.1, 276

[56] References Cited

U.S. PATENT DOCUMENTS

| | | | |
|---|---|---|---|
| 3,839,172 | 10/1974 | Chapiro et al. | 525/276 |
| 4,143,218 | 3/1979 | Adams et al. | 427/430.1 |
| 4,743,258 | 5/1988 | Ikada et al. | 623/1 |
| 4,877,839 | 10/1989 | Conti-Ramsden et al. | 525/276 |
| 4,897,433 | 1/1990 | Sugo et al. | 427/2 |

FOREIGN PATENT DOCUMENTS

2035350 6/1980 United Kingdom ............ 623/1

Primary Examiner—Norman Morgenstern
Assistant Examiner—Terry J. Owens

[57] ABSTRACT

A surface for the attachment and growth of cells is prepared by first grafting polyacrylic acid chains to a fluorocarbon polymer substrate so that its weight increases by between 0.1% and 20%. The surface is then treated with concentrated sulphuric acid under such conditions that will separately decarboxylate, aromatize and sulphonate an effective proportion of the grafted polyacrylic acid chains before being dried, soaked in a concentrated acid and brought to a substantially neutral pH for cell attachment and growth thereupon. The surface may also be used as a human tissue implant.

17 Claims, 7 Drawing Sheets

MATERIAL FOR CELL ATTACHMENT AND GROWTH

FIELD OF INVENTION

This invention relates to the chemical modification of polytetrafluoroethylene (PTFE, which is sold under the Registered Trade Mark TEFLON) and other fluorocarbon polymers, to produce a surface that is a suitable substratum for the attachment and growth of adherent animal cells.

The invention also relates to chemical procedures to achieve this modification of PTFE and other fluorocarbon polymers and to procedures for the preparation of the chemically modified surface for cell attachment. Particular attention is drawn to the ability of PTFE modified by these procedures to serve as a substratum for the attachment and growth of human endothelial cells, and so to the potential use of these chemically modified fluorocarbon polymers and procedures in the preparation of implantable materials including vascular prostheses and percutaneous implants.

BACKGROUND ART

Information gained during in vitro cell culture experiments can profitably be used in the design or selection of materials for use in specific biomaterials such as vascular prostheses. The attachment and growth of endothelial cells and other anchorage-dependent animal cells during in vitro cell culture requires both a suitable substratum for cell attachment and a culture medium that contains either serum, or certain purified serum proteins.

Concerning the chemical nature of the substratum, cells such as endothelial cells do not attach and grow well on hydrophobic surfaces such as nonwettable polystyrene (bacteriological plastic) or on PTFE which is commonly used in vascular prosthetic grafts. On the other hand, cells including endothelial cells also fail to adhere to many hydrophilic polymers, such as the hydrogel poly-2-hydroxyethylmethacrylate, polyHEMA. Cells do attach and grow on polymers where the surface is composed of microdomains containing both hydrophobic and hydrophilic regions. The use of polymers with a microdomain structure of this nature is now the state of the art in the biomedical material area (e.g. the polyurethanes sold under the Registered Trade Marks BIOMER and MITRATHANE). The perfluorosulphonate ionomer which is known by the Registered Trade Mark NAFION has recently been shown to be suitable for endothelial cell attachment and growth (International patent application PCT/AU88/00368; McAuslan et al., (1988) J. Biomed. Mater. Res., 22,963-976; Norris et al., (1988) Clinical Materials, 3,153-162; and may also fit this generalisation, in that as only 1 in every 8 monomer units is sulphonated, the large segments of uncharged chains may allow for both hydrophobic and hydrophilic interactions.

The surface that is commonly used for animal cell attachment and growth in vitro is polystyrene, modified by one of a number of techniques to produce a surface that can promote cell attachment (tissue culture polystyrene). This modification of polystyrene has been performed by treatment with sulphuric acid (Kennedy & Axelrod, (1971) Immunology, 20,253-257); with chromic acid or with sulphuric acid and chromic acid (Klemperer & Knox, (1977) Laboratory Practice 26(3), 179-180); or treatment with a corona discharge process (Maroudas, (1973) in "New Techniques in Biophysics and Cell Biology" (R. H. Payne and B. J. Smith, eds) Wiley Interscience, London). These treatments are believed to introduce hydroxyl groups, and the surface concentration of hydroxyl groups must fall within a range for the polystyrene derivative to be suitable for cell attachment (Curtis et. al., (1983) J. Cell Biology 97, 1500-1506; and Curtis et. al. (1986) J. Cell Sci. 86,9-24). Carboxyl groups produced in the reactions appear to play only a small role in the cell adhesion to modified polystyrene (Curtis et al., 1986). Very few sulphonate groups are introduced into the surface (Curtis et al. 1983).

Somewhat different results as to the surface groups required for cell attachment were obtained in a study of cell attachment to polyHEMA by McAuslan et al (PCT/AU87/00043 and McAuslan et al., J. Biomed. Mater. Res., 1987). In that study it was shown that hydrolytic etching of polyHEMA with sulphuric acid converted the non-adhesive surface into a surface that is highly adhesive for cells. In that case, the improvement in adhesiveness of the hydroxyl-rich surface of polyHEMA surface for cells appeared to correlate with the partial introduction of carboxyl groups onto the surface.

Another aspect of the mechanism of adhesion of cells to polymeric surfaces is that serum adhesive proteins adsorbed to the surface contribute to the cellular attachment reaction. For tissue culture polystyrene, the serum component fibronectin (Fn) has been shown to support endothelial cell attachment. Recent results from Underwood et al. (Aust. New Zealand Soc. Cell Biol., 1988 Meeting, abstracts 1988) point to the adsorption to the polystyrene surface of a second serum component, vitronectins as being essential to the attachment of endothelial cells. The nature of the surface chemistry can have subtle effects on the conformation of the attached serum components with consequential effects on the biological potency of the adsorbed protein. Grinnel and Feld (1981) J. Biomed. Mater. Res., 15, 363-381 and (1982) J. Biol Chem., 257, 4888-4893; have compared the binding of fibronectin to tissue culture polystyrene and biological potency of the bound fibronectin with the binding to hydrophobic unmodified polystyrene. That study showed that the ability of the fibronectin adsorbed to the tissue culture polystyrene surface to promote cell attachment was markedly greater than that of fibronectin adsorbed to the hydrophobic polystyrene surface. It follows that the suitability of a polymer surface for cell attachment is related to both the surface chemistry and to the ability of the surface to adsorb specific adhesive proteins (whether from the serum or as purified serum components) in an active conformation.

The luminal surface of natural blood vessels has an antithrombogenic character which is believed to be a direct consequence of the ability of the endothelial cells that line the vessel to resist thrombus formation. Synthetic vascular grafts have a markedly more thrombogenic surface and frequently fail because of spontaneous thrombosis. It is believed that if the surface of the graft can be covered with endothelial cells that function physiologically, these cells will form a naturally nonthrombogenic interface between the graft and the blood. The cells that are involved in such a process of endothelialisation could arise through spontaneous coverage from endogenous sources (migrating endothelial cells from cut edges of the adjacent blood vessel, or else from capillaries migrating from the perigraft tissue through the interstices of a porous graft) or by seeding of the graft with endothelium. One aspect of the design of vascular prostheses is therefore to ensure that endothelial cells can attach and grow on the surface, particularly where the graft is for use in small to medium-sized arteries that carry low blood flow. Thus the ability of the polymer surface to support endothelial cell attachment and growth is an important characteristic of the effectiveness of the prosthesis. Surfaces that are suitable for endothelial cell attachment and growth are likely to support ingrowth of other mesenchymal tissues, and so be suitable for general implant applications including the enhancement of wound closure and anchorage of percutaneous implants.

The failure of the hydrophobic surface of PTFE to adequately support cell attachment, including attachment of endothelial cells exposed to the shear forces involved in blood flow, is a limitation to the use of this material for vascular prostheses. If PTFE could be modified to produce a surface that supported enhanced endothelial cell attachment and growth, the modified surface could be expected to be more suitable than unmodified PTFE for the process of in vivo endothelialisation. PTFE that is modified to be superior to unmodified PTFE for the attachment of endothelial cells would certainly be preferable for use in the new approach (Herring, Gardner and Glover, (1978) Surgery, 84, 498–504) of preseeding grafts with endothelial cells prior to implantation.

While the introduction of strongly bonded surface carboxyl groups to normally hydrophobic fluorocarbon polymers by various high energy techniques of grafting is well known (eg Charpiro & Jendrychowska-Bonamour (1980) Polymer Engineering and Science, 20(3), 202–205) we have found that the resultant surface poorly supports endothelial cell growth. It appears that the even distribution of carboxyl groups provided by these grafting methods is not beneficial to cell attachment, when quite low (around 1%) grafting levels or higher levels are used. In contrast to this finding and the lack of cell attachment to unmodified PTFE and other fluorocarbon polymers, it has now been found by the present inventors that acidic treatments of PTFE and other fluorocarbon polymers to which polyacrylic acid chains have been grafted produce surfaces having improved cell attachment and growth properties, without adversely affecting the physical properties of the materials.

Accordingly, the present invention is centred on the development of processes for the chemical modification of PTFE and other fluorocarbon polymers, to produce an implantable surface that supports the attachment and growth of animal (including human) tissue cells, such as fibroblasts and other mesenchymally-derived cells, epithelial cells and endothelial cells. Where it is endothelial cells in contact with the fluoropolymer surface, the surface produced by this process would support the attachment and growth of the endothelial cells into a confluent surface. The attached endothelial cells then present at the blood interface an antithrombogenic surface which inhibits undesirable platelet interactions.

DISCLOSURE OF THE INVENTION

It is an object of the present invention to provide a material useful in implantable prostheses which will substantially overcome the disadvantages of the prior art in that it has improved biocompatibility arising from enhanced cell attachment properties and antithrombogenicity.

According to the invention there is provided a process for preparing a surface for the attachment and growth of cells, said process comprising the steps of:
(i) grafting polyacrylic acid chains to a fluorocarbon polymer substrate so that the weight of the fluorocarbon polymer substrate increases by between 0.1% and 20%,
(ii) treating the fluorocarbon polymer surface produced by step (i) with concentrated sulphuric acid at a sufficiently high temperature and for a time to separately decarboxylate, aromatize and sulphonate an effective proportion of the grafted polyacrylic acid chains,
(iii) drying the surface produced by step (ii),
(iv) soaking the surface produced by step (iii) in a concentrated acid,
(v) neutralizing the surface produced by step (iv).

Optionally, the grafted substrate produced by step (i) may be left to soak in room temperature sulphuric acid prior to the treatment of step (ii). This is best done overnight.

Where required, the neutralized surface produced by step (v) may be treated with serum, cell attachment factors derived from serum or connective tissue (such as fibronectin or vitronectin) or with tissue growth factors.

The preferred method of grafting polyacrylic acid chains to the substrate in step (i) is by gamma-irradiation grafting. Other means of grafting, such as laser grafting, may be employed where appropriate. Where gamma-irradiation grafting is employed, step (i) is preferably carried out according to the method of Charpiro (reviewed in Charpiro & Jendrychowska-Bonamour, 1980) which involves treatment of the polymer surface with a water soluble inhibitor in the grafting solution.

The time required to seperately decarboxylate, aromatize and sulphonate an effective proportion of the grafted polyacrylic acid chains of the surface in step (ii) will depend on the temperature at which the sulphuric acid treatment of the polymer is carried out, but it is preferred that the treatment of step (ii) is with sulphuric acid at 105° C. for 2 hours. It is understood by the skilled artisan that an effective proportion of grafted polyacrylic acid chains refers to that proportion of same that will lead to effective attachment and growth of cells on the surface of the invention.

Preferably, the drying that is required in step (iii) is carried out by heating at 105° C. for 4 hours, while the soaking in concentrated acid that is required in step (iv) is preferably carried out with concentrated nitric acid at room temperature for 4 hours.

Neutralization of the relatively acidic surface produced by step (v) is preferably carried out by washing with phosphate buffered saline at pH 7.4.

According to another aspect of the invention, there is provided a surface for the attachment and growth of cells whenever prepared by any one of the aforementioned processes.

According to a further aspect of the invention, there is provided a method of promoting cell attachment and growth on a surface comprising preparing a surface according to any one of the aforementioned processes and exposing said surface to cells.

The preferred fluorocarbon polymers of the substrate include polytetrafluoroethylene, fluorinated ethylene propylene, polychlorotrifluoroethylene and polyvinylidine fluoride which may readily be gamma-irradiation grafted with polyacrylic acid chains. The polyacrylic acid chains that are grafted onto the substrate in this manner may be the product of reaction of the substrate with acrylic acid or acrylate ester.

Where gamma-irradiation grafting has been employed in step (i) the chemical changes to the surface produced after step (iv), in which step concentrated nitric acid has been used, have been studied by electron spectroscopy for chemical analysis (ESCA). This study shows that small concentrations of surface sulphur groups (probably sulphonic acid) at a binding energy of 167 eV (for S 2p) are present and that the number of these increases with the time and temperature of acid treatment. Preferably, the surface produced after step (iv) will contain about 1 sulphur atom per 75 carbon atoms.

Fourier Transform Infrared (FTIR) studies of the treated PTFE surfaces (by Attenuated Total Reflectance ATR) showed that considerable decarboxylation of the acid groups at 1710 cm$^{-1}$ had occurred in the 1 micron surface layer, but that other non-ionizable, oxidized species had partly taken their place (broad peaks at 1720–1670 cm$^{-1}$).

ESCA studies comparing the grafted surface produced by step (i) with the surface after step (iv) further showed that the surface carboxyl groups at binding energy of 288 eV are present at 1/5 of the equivalent levels of CF groups at binding energy of 292 eV in the surface after step (i). The level of these surface carboxyl groups decreases during treatment at room temperature and at 105° C. with sulphuric acid but is not significantly modified during the drying step (iii). Some re-oxidation of carbon to give further carboxyl groups occurs during step (iv). After step (iv), the carboxyl group signal had diminished to approximately 70% of the peak height of the original carboxyl peak (288 eV) observed after step (i).

The ion exchange capabilities dropped from 1.2 meq/g in the original grafted films to 0.82 meq/g for 10 mins treatment, 0.75 meq/g for 18 mins and 0.26 meq/g for the optimum treatment period of over 1 hr. The time to reach the measured equilibrium ion exchange capabilities increased from 1 hr to 24 hrs due to this surface decarboxylation. Ultraviolet and visible spectroscopy indicated that aromatization of the polyacrylic acid graft occurred, with an increase on treatment in the broad adsorption peak from below 25 nm to above 430 nm; adsorption values above 1.0 in the PTFE (Quinton cannula connector) tubes moved from about 305 nm to 550 nm. In line with the above changes, the ESCA studies showed that the ratio of unfluorinated carbon atoms (i.e. carbons from the acrylic acid grafted on during step (i)), decreased when compared to fluorinated carbons, during the treatment with sulphuric acid in step (ii). The number of sulphur atoms increased from negligible to be about 1 in 75 of the C atoms following step (ii), and remained at this level in subsequent treatments during steps (iii), (iv) and (v). None of these changes occurred with similar treatments of ungrafted PTFE film or tubing.

DESCRIPTION OF PREFERRED EMBODIMENTS

In order that the invention may be more readily understood and put into practical effect, reference will now be made to the following examples.

EXAMPLE 1

Chemical modification of PTFE film and modification of PTFE tubes (TEFLON Cannula Connector tubes)

A portion of polytetrafluoroethylene film (200 microns thick) was cut into 5cm$^2$ pieces and soaked in a solution of acrylic acid, 10% in methylene chloride, for 2 days. The samples were removed and air dried before being placed in a suitable glass vessel containing a grafting solution of 10 g of acrylic acid in 90 g of distilled water containing 0.03% CuCl$_2$. The samples were then irradiated for 16 hrs at a dose rate of approximately 0.07 MRad/hr (total dose=1.12 MRad) in a Cobalt 60 source, to give 1.25% by weight of grafted polyacrylic acid on the PTFE. The grafted film was then cleaned in distilled water, dried and then placed in concentrated sulphuric acid at 105° C. for 90 mins. The light brown film was then washed in distilled water, dried at 90° C. for 16 hrs, and finally cleaned in concentrated nitric acid by soaking for 24 hrs. Prior to tissue culture studies the pieces were extensively washed in sterile phosphate buffered saline (PBS) pH 7.2. These pieces of modified PTFE film were subsequently used in Example 3.

Twenty cannula connector tubes (Catalog no. 11150-002 from Quinton Instrument Co., Seattle, Wash. 98121, described as tubes of plain non-etched PTFE of 25 mm length, 2.8 mm I.D., 3.4 mm O.D.) were soaked in a solution of acrylic acid, 10% in methylene chloride, for 2 days before being air dried and placed in the grafting solution of acrylic acid 10% in 0.03% aqueous $CuCl_2$ solution. These were gamma-irradiation treated at a dose rate of approximately 0.07 MRad/hr for 16 hrs (total dose 1.12 MRad) to give a 1.5% by weight graft on the tubes. The grafted tubes were then cleaned in distilled water, dried, allowed to soak overnight in sulphuric acid at room temperature and then placed in concentrated sulphuric acid at 105° C. for varying periods of time, to give surfaces with different characteristics. Treatment with sulphuric acid for 90 minutes was used to produce mPTFE tube sample #1, whereas treatment for 15 minutes was used to produce mPTFE tube sample #2. The tubes had different colours depending upon the treatment time, varying from light brown in colour (mPTFE tube sample #2) to a darker brown (mPTFE tube sample #1). These tubes were then washed in distilled water, dried at 90° C. for 16 hrs and finally treated with concentrated nitric acid by soaking for 24 hrs. Other grafted cannula connector tubes were treated with sulphuric acid at 105° C. for 2 hr, then dried at 105° C. for 4 hr, then soaked with room temperature nitric acid for 4 hr and then washed in distilled water (these are mPTFE tube samples #3a). Prior to tissue culture studies all the tube samples were extensively washed in sterile PBS. These modified PTFE tubes were subsequently used in Example 2.

EXAMPLE 2

Attachment and Growth of Ovine Endothelial Cells On Modified PTFE Tubes

Methods

PTFE Cannula connector tubes which were modified by the procedure specified in Example 1 were sonicated in acetone and washed in 70% ethanol. The mPTFE tubes required pH equilibration prior to use, by incubation with several changes of serum-free culture medium until a stable pH was detected. (No further change in the colour of the pH indicator in the medium over a period of more than 1 hr was deemed sufficient evidence of pH stability). Some of the mPTFE samples #3a were pre-coated with fibronectin (Fn) from bovine plasma by being aseptically filled with a solution of 40 ug/ml Fn in PBS, plugged and incubated at 37° C. for 1 hr prior to cell seeding (these are mPTFE tube samples #3b).

An ovine carotid arterial endothelial cell culture (OCAE) was established after the methodology of Jaffe ((1984) in "Biology of Endothelial Cells" (E. A. Jaffe, ed) Martinus Nijhoff, Boston), and routinely maintained in McCoy 5A (modified) medium supplemented with 20% foetal bovine serum, 60 ug/ml penicillin and 100 ug/ml streptomycin and passaged using trypsin-versene. For experimental work cells were used between passage 5 and passage 12 (inclusive). Preequilibrated mPTFE tubes were individually placed into sterile, screw-cap polystyrene vials, then 9 ml of growth medium containing $2 \times 10^6$ cells was added to each vial. The cell suspension was gassed with a mixture of 5% $CO_2$ in air and the vial tightly sealed. The vials were then placed inside a TCP roller bottle and firmly held in position by packing. The loaded bottle was then rotated at 1 r.p.m. on a roller at 37° C. The culture medium was replenished at 24 hr and 72 hr and the tubes removed for subsequent flow-testing after 5 days.

Visualisation of progressive cell growth necessitated the removal of a 5 mm long end section of selected tubes which were then fixed in a 2.5% (v/v) of glutaraldehyde in PBS, (GLUT), stained with Eosin Y and viewed under fluorescence microscopy. The cells were observed using an Olympus IMT microscope with a reflected light fluorescence attachment. Other tubes supporting cell attachment and growth were cultured for 6 hr in culture medium consisting of Dulbecco's modified Eagle's medium containing glutamine, 3 mg/l methionine and 25 uCi/ml of 35S-methionine, then further incubated with McCoys 5A medium with serum and supplements for a further 15 hr. The tubes containing the metabolically-labelled cells were briefly washed in PBS then inserted into the flow test system as shown in FIG. 1.

Figure 1:
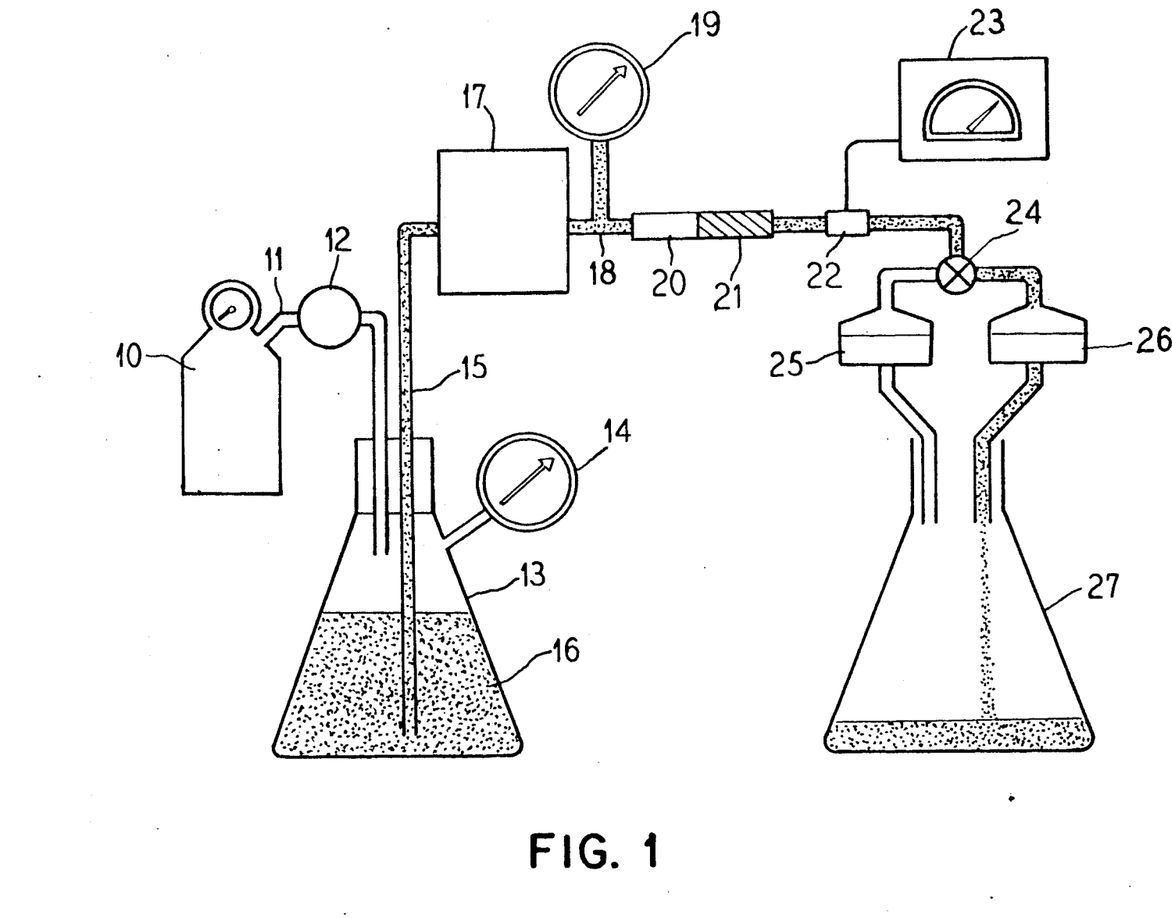
FIG. 1 is a schematic view of the flow test system used in the Examples.

The flow test system of FIG. 1 includes a gas cylinder 10 having a cylinder outlet 11 that passes through gas flow regulator 12 and delivers gas to a vacuum flask 13 having an air pressure manometer 14. A tube 15 feeds from the cell culture medium 16 in the flask 13 to a water bath 17 held at 37° C. A bath outlet tube 18 has a media pressure manometer 19 connected thereto and downsteam of the tube 18 is a flow adaptor tubing 20 and the subject graft 21 (in this case, the prepared tubes). Further downstream is a flow probe 22 connected to a flow meter 23. The tube 18 terminates at a three-way tap 24 from where the tube 18 forks to a pair of glass fibre filters 25 and 26. Material not captured by the filters is collected in the flask 27.

The tubes were subjected to increasing flow rates of a medium consisting of McCoys 5A medium containing 20 mM Hepes buffer (pH 7.2) and 20% (v/v) foetal bovine serum at 37° C. for the specified time periods. Cells released from the tube and that were collected on the downstream filters were quantitated by radioactive determination (liquid scintillation counting). Following the flow studies, the tube was removed and bisected, then half of the tube was examined for adherent cells by microscopic techniques and the cells on the other half were removed using trypsin-versene and the radioactivity in the released cells was determined.

RESULTS

Figure 2A:
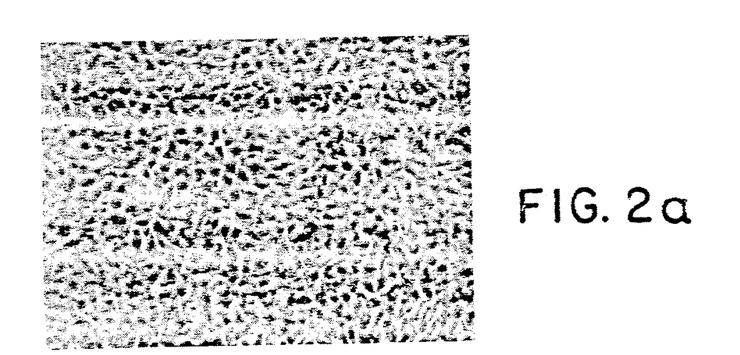
FIG. 2(a) is a photomicrograph of ovine carotid arterial endothelial (OCAE) cells grown on modified sample #1 of a surface of the invention.
Figure 2B:
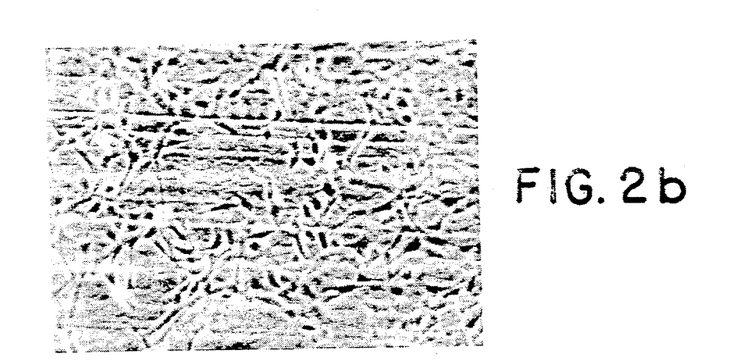
FIG. 2(b) is a photomicrograph of OCAE cells grown on modified sample #2 of a surface of the invention.
Figure 2C:
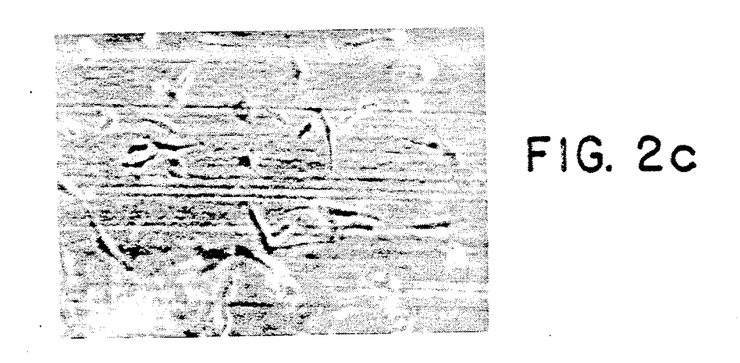
FIG. 2(c) is a photomicrograph of OCAE cells grown on unmodified PTFE surfaces.
Figure 2D:
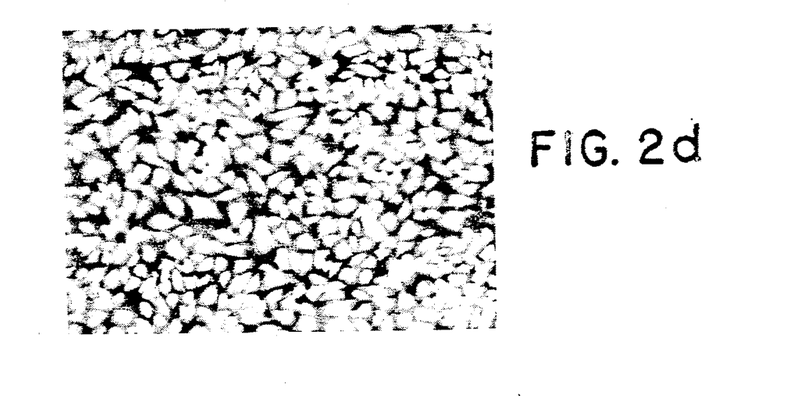
FIG. 2(d) is a photomicrograph of OCAE cells grown on modified sample #3a of a surface of the invention.

OCAE cell growth was studied on mPTFE tubes that had four levels of surface modification (mPTFE samples #1, #2, #3a and #3b, which had the same level of acrylic acid graft but which had subsequently been exposed to different post-graft modification conditions, as earlier specified. The cell growth on these tubes was compared to that on unmodified PTFE cannula connectors.

mPTFE tube samples #1, #3a and #3b which were exposed to longer periods of post-grafting modification than was mPTFE tube sample #2, supported good OCAE cell growth. The cell monolayer on sample #1 reached confluent levels by 3 days (see FIG. 2a), and at 5 days showed no signs of cell layer delamination or clumping. However on mPTFE tube sample #2, the cells did not reach confluence by day 5, and many of the cells tended to clump together, whilst others displayed a spindle-like morphology (see FIG. 2b for morphology after 3 days). The unmodified PTFE tubes supported very little OCAE cell attachment and growth, with those few cells that were present showing very poor cell spreading (see FIG. 2c). mPTFE tube sample #3a supported good cell attachment and growth of OCAE cells, (See FIG. 2d) and a similar result was achieved with mPTFE sample #3b (not shown).

These results demonstrate that chemical modification of PTFE tubes in the manner described for tube samples #1, #3a and #3b produced surfaces that were markedly better than unmodified PTFE tubes for initial OCAE cell attachment and growth.

FLOW TESTING mPTFE tubes were prepared similarly to tube sample #1, seeded with OCAE cells which formed a confluent layer after 5 days growth on their luminal surface, and were tested in an in vitro flow system (See Table 1, experiment Nos. 1 to 6). The OCAE cells withstood the shear force treatments of up to 4 dynes/cm$^2$, with a minimum of 73% of the cells remaining attached to the tube, and with less than 7% of the cells being lost from the surface in 4 of the 6 experiments. mPTFE tubes prepared similarly to tube samples #3a and #3b were seeded with OCAE cells, and these cells withstood shear force treatments of up to 20 dynes/cm$^2$ (Experiment Nos. 7 to 15 of Table 1) which is equivalent to shear force levels found in arterial blood vessels. A minimum of 94.3% of the cells remained attached to tube sample #3a as shown in Experiment Nos. 7 to 10, whilst a minimum of 92.5% of the cells remained attached to sample #3b as shown in Experiment Nos. 11 to 15. These experiments show that endothelial cells form strong attachment to the mPTFE surface.

TABLE 1

| | Retention of OCAE cells on mPTFE tubes under fluid flow conditions | | |
|---|---|---|---|
| Experiment | Flow protocol | % cells remaining attached | % cells detached and recovered on filters |
| 1 | a | 73.0 | 27.0 |
| 2 | a | 98.1 | 1.9 |
| 3 | a | 81.0 | 19.0 |
| 4 | b | 93.9 | 6.1 |
| 5 | b | 97.6 | 2.4 |
| 6 | c | 98.1 | 1.9 |
| 7 | d | 97.4 | 2.6 |
| 8 | d | 94.7 | 5.3 |
| 9 | d | 96.7 | 3.3 |
| 10 | d | 94.3 | 5.7 |
| 11 | d | 97.7 | 2.3 |
| 12 | d | 96.4 | 3.6 |
| 13 | d | 92.5 | 7.5 |
| 14 | d | 97.8 | 2.2 |
| 15 | d | 97.1 | 2.9 |

Experiment Nos. 1 to 6 utilize tube sample #1, experiment Nos. 7 to 10 utilize tube sample #3a and experiment Nos. 11 to 15 utilize tube sample #3b.

Cells were subjected to the following flow protocols:
a: 10 min at 14 ml/min (0.8 dynes/cm$^2$) then 10 min at 38 ml/min (2.3 dynes/cm$^2$) then 10 min at 70 ml/min (4.0 dynes/cm$^2$).
b: 5 min at 38 ml/min then 10 min at 56 ml/min then 9 min at 70 ml/min.
c: 10 min at 38 ml/min then 10 min at 56 ml/min then 6 min at 70 ml/min.
d: 10 min at 66 ml/min (4.0 dynes/cm$^2$) then 10 min at 132 ml/min (8 dynes/cm$^2$) then 10 min at 198 ml/min (12 dynes/cm$^2$) then 10 min at 264 ml/min (16 dynes/cm$^2$) then 10 min at 330 ml/min (20 dynes/cm$^2$).

EXAMPLE 3

Attachment and Growth of Human Endothelial Cells On Modified PTFE Film

Methods

Sheets of unmodified, virgin PTFE and PTFE modified by the procedure specified in Example 1 above, (mPTFE), were cut into squares of approximately 5mm×5 mm, sonicated in acetone then washed extensively in 70% ethanol for 2 hr. The mPTFE required pH equilibration and stabilisation prior to use, and equilibration was achieved with several changes of serum-free growth medium until a stable pH was detected. Those samples to be coated with fibronectin (Fn) were each placed into a 22 mm diameter TCP well (12-well cluster dish) and covered with 1 ml of a solution of 40 ug/ml Fn in PBS and incubated at 37° C. for 1 hr.

A human umbilical artery endothelial cell culture (HUAE) was established and grown in 75 cm$^2$ tissue culture polystyrene (TCP) flasks coated with Fn. Fn coating was achieved by incubating the flasks with 5 ml solution of 40 ug/ml Fn in PBS at 37° C. for 1 hr prior to cell seeding. The cells were routinely maintained in a growth medium consisting of an equal mixture of McCoy 5A (modified) and BM86-Wissler media supplemented with 30% v/v foetal bovine serum, 40 ng/ml fibroblast growth factor, 60 ug/ml endothelial cell growth supplement, 20 ug/ml insulin, 60 ug/ml penicillin and 100 ug/ml streptomycin. The cells were routinely passaged using trypsin-versene, and for experimental work cells were used between passage 15 and passage 20 (inclusive).

For cell growth studies, pre-equilibrated samples were individually placed into 22 mm diameter TCP wells and 2 ml of the growth medium earlier used to maintain the HUAE cell culture containing 5×10$^4$ cells was added to each well.

In some experiments of this Example, the serum adhesive glycoprotein fibronectin was removed from the foetal bovine serum component of the growth medium prior to use of the growth medium in the cell growth studies by passage over a gelatin-Sepharose affinity column. Serum treated on a gelatin-Sepharose column was confirmed to be free of fibronectin by immunoassay of the fibronectin content. In other experiments, the serum adhesive glycoprotein vitronectin was similarly removed by passage over an affinity column consisting of immobilized anti-vitronectin monoclonal antibody. The sera that were depleted of vitronectin by this affinity technique were confirmed to have been exhaustively stripped of vitronection by immunossay of vitronectin content.

TCP and Fn-coated TCP were used as control surfaces, with particular attention being paid to Fn coated TCP, which is known to support good HUAE cell attachment and growth. Duplicates of each test sample were fixed in GLUT at 24, 72 and 120 hr, then stained with a 0.05% aqueous solution of Eosin Y, and viewed by fluorescence microscopy. Ten random fields per test sample were photographed and the mean and standard error of cell number per cm$^2$ were determined from photographic prints.

Results

The number of HUAE cells attached to the mPTFE surface as viewed 24 hr after cell seeding was approximately 88% of that on TCP whereas for unmodified PTFE the number of cells attached was 74% of that on TCP—see Table 2.

TABLE 2

| HUAE cells attached/cm2 after 24 hr. | |
| --- | --- |
| Substrate | Mean cell no./cm2 ± (S.E.M.) |
| TCP | 2012 ± (141) |
| PTFE | 1489 ± (179) |
| mPTFE | 1771 ± (333) |
| TCP/Fn | 3817 ± (292) |
| PTFE/Fn | 3037 ± (202) |
| mPTFE/Fn | 4000 ± (343) |

The morphology of the HUAE cells on mPTFE was generally quite elongated and spindle-like. This morphology indicated that although some cell spreading processes had occurred, the cells had not spread to form the well spread morphology that is typical of well attached endothelial cells. The morphology of the HUAE cells on the mPTFE was generally similar to that on TCP after 24 hr. By comparison, HUAE cells that had been seeded and attached on unmodified PTFE were mainly truncated or rounded up, clearly showing that the attachment of individual cells on the mPTFE was better than on the unmodified PTFE surface.

Figure 3A:
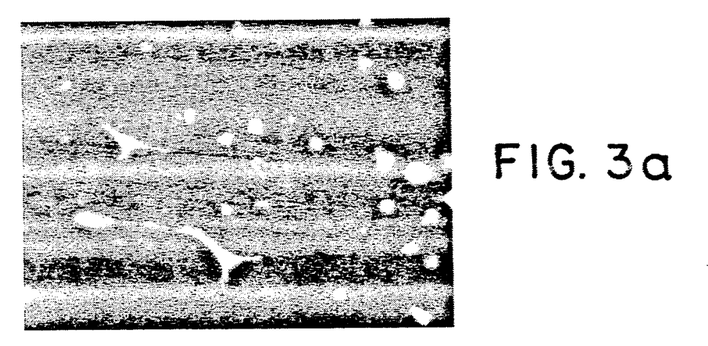
FIG. 3(a) is a photomicrograph of human umbilical artery endothelial (HUAE) cells grown for 24 hours after seeding onto mPTFE in serum-free medium.
Figure 3B:
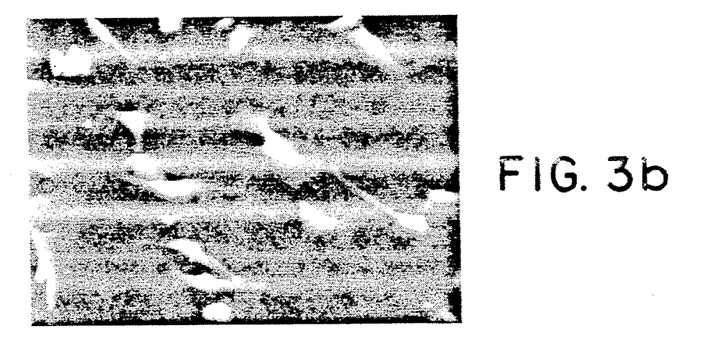
FIG. 3(b) is a photomicrograph of HUAE cells grown for 24 hours after seeding onto mPTFE in medium containing serum.
Figure 3C:
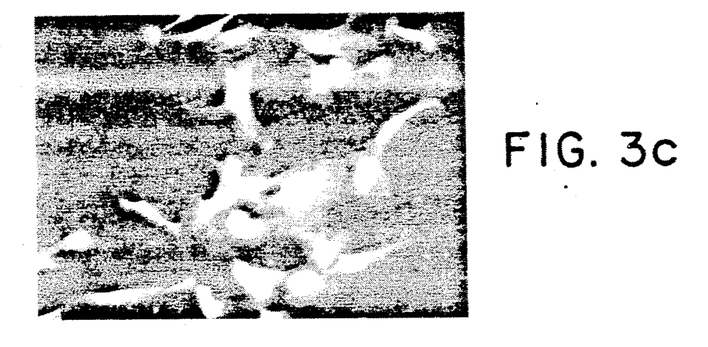
FIG. 3(c) is a photomicrograph of HUAE cells grown for 24 hours after seeding onto mPTFE in medium containing Vitronectin-stripped serum.
Figure 3D:
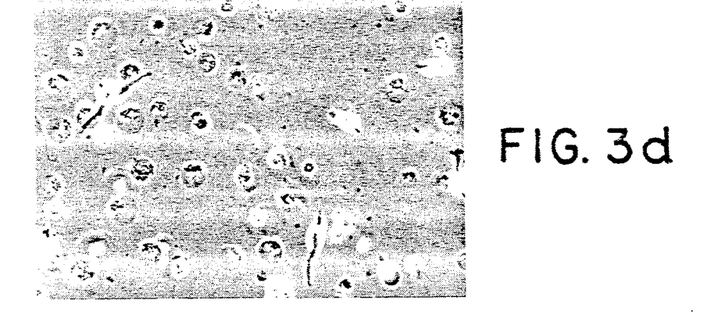
FIG. 3(d) is a photomicrograph of HUAE cells grown for 24 hours after seeding onto TCP in serum-free medium.
Figure 3E:
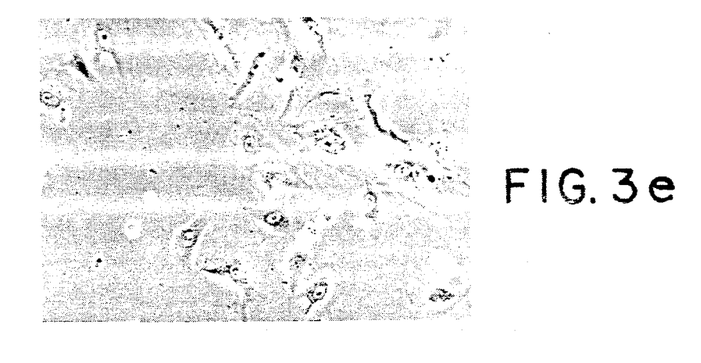
FIG. 3(e) is a photomicrograph of HUAE cells grown for 24 hours after seeding onto TCP in medium containing serum.
Figure 3F:
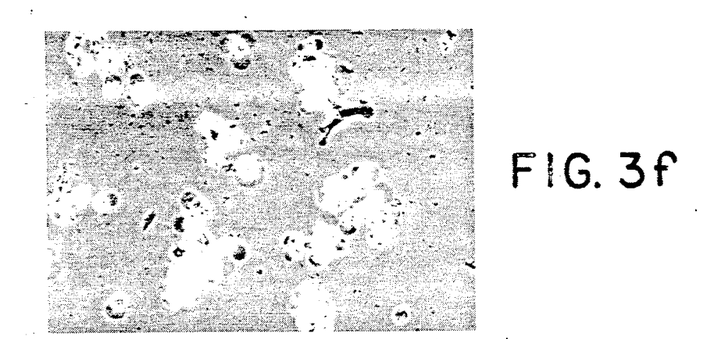
FIG. 3(f) is a photomicrograph of HUAE cells grown for 24 hours after seeding onto TCP in medium containing Vitronectin-stripped serum.

The role that the serum component of culture medium may play in the attachment of HUAE cells to mPTFE and to tissue culture plastic was determined. When the culture medium in which the HUAE cells were seeded did not contain serum, the HUAE cells did not spread on either mPTFE or TCP surfaces (see FIG. 3a and d). The role that serum adhesive glycoproteins fibronectin and vitronectin may play in the attachment of HUAE cells to mPTFE was determined by selectively depleting the serum component of the culture medium of fibronectin or vitronectin by passage over an affinity chromatography matrix. Selective removal of fibronectin from the serum component of the culture medium did not interfere with HUAE cell attachment and spreading onto mPTFE or onto TCP. Selective removal of vitronectin from the culture medium caused reduced cell attachment to the TCP surface with the attached cells being unable to spread onto the surface (FIG. 3e as compared to FIG. 3f). When HUAE cells were seeded onto the mPTFE surface in medium containing serum depleted of vitronectin, the HUAE cells did attach and spread, to an extent that was equivalent to that on mPTFE with intact serum (compare FIG. 3b with c). The importance of vitronectin, which is also known as serum spreading factor, epibolin or 70K spreading factor, has previously been reported for polymer surfaces such as tissue culture polystyrene (see Grinnell (1976) Exp. Cell Res., 97, 265–274 and (1977) Exp. Cell Res., 110, 175–190; Underwood and Bennett (1989) J. Cell Science (in press, 1989)) and Nafion (International patent application No. PCT/AU88/00368). These results indicate that vitronectin is not essential for attachment of HUAE cells to the mPTFE surface, unlike the TCP surface. These results do not exclude the possibility that serum vitronectin adsorbed onto the mPTFE surface may contribute to HUAE cell attachment and spreading onto mPTFE when the culture medium contains serum.

Figure 4:
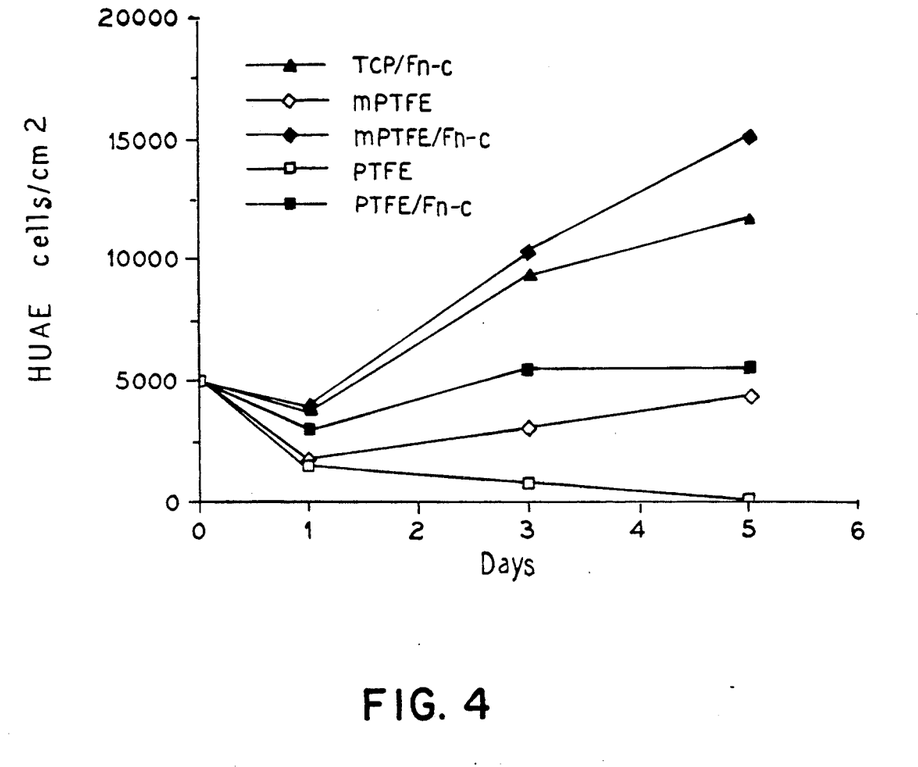
FIG. 4 is a graph of HUAE cell growth over 5 days on various surfaces of Example 3.
Figure 5A:
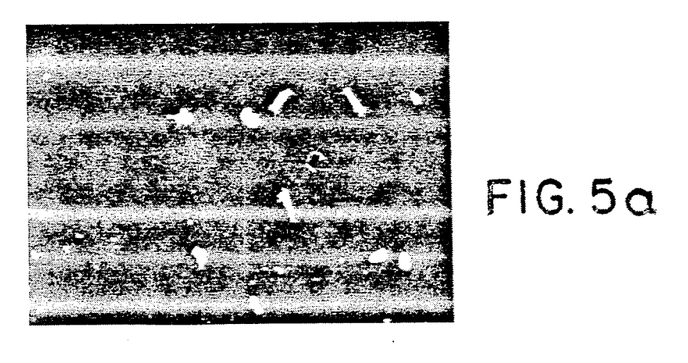
FIG. 5(a) is a photomicrograph of HUAE cells grown for 3 days on PTFE.
Figure 5B:
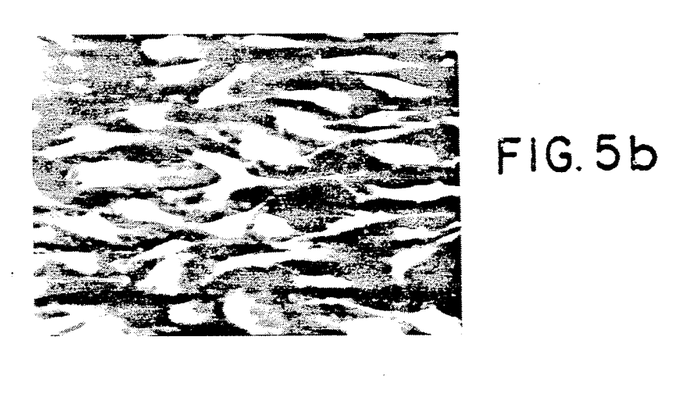
FIG. 5(b) is a photomicrograph of HUAE cells grown for 3 days on mPTFE.

Subsequent growth over a 5 day period was monitored (see FIG. 4) and FIGS. 5(a) and (b) show the morphology on PTFE and mPTFE respectively after 3 days growth. These studies showed that cell growth occurred slowly on the mPTFE surface, whereas on unmodified PTFE there was very poor cell growth, and cell numbers reduced to a point where very few cells were visible after 72 hr, and no cell attachment was evident after 5 days.

Figure 6A:
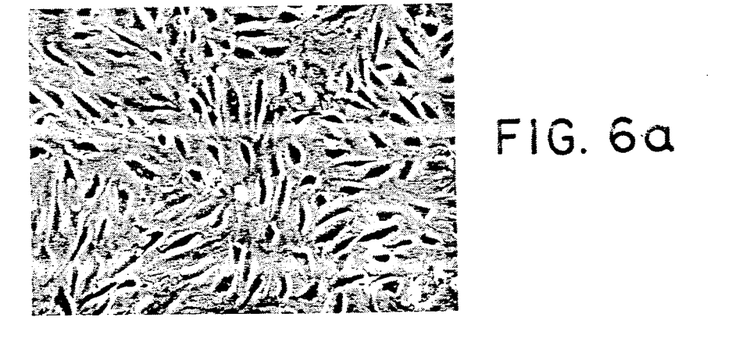
FIG. 6(a) is a photomicrograph of HUAE cells grown for 3 days on Fibronectin-coated TCP.
Figure 6B:
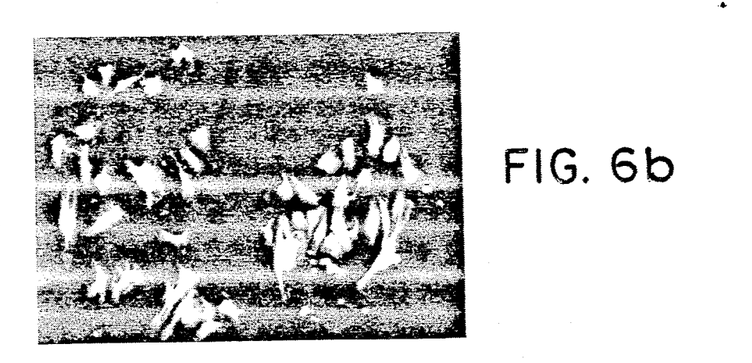
FIG. 6(b) is a photomicrograph of HUAE cells grown for 3 days on Fibronectin-coated PTFE.
Figure 6C:
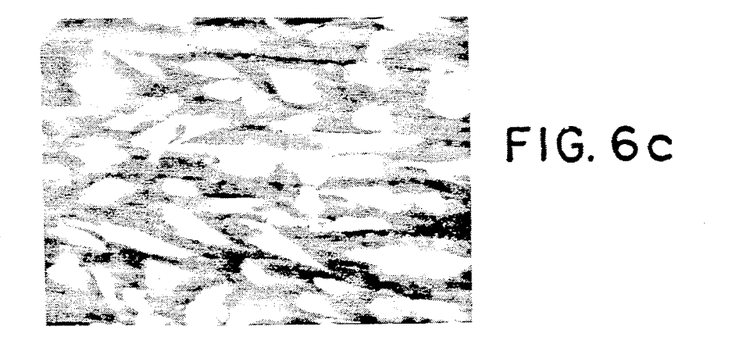
FIG. 6(c) is a photomicrograph of HUAE cells grown for 3 days on Fibronectin-coated mPTFE.
Figure 6D:
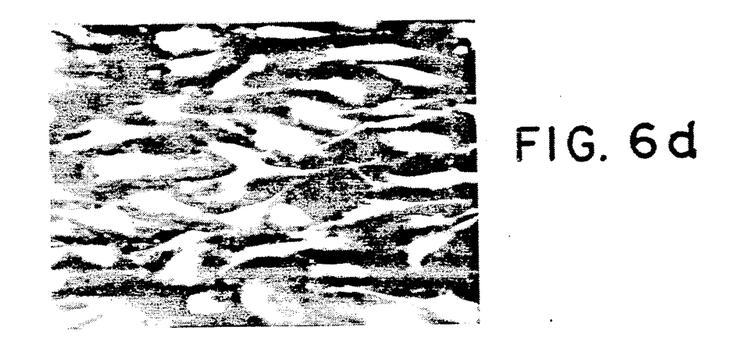
FIG. 6(d) is a photomicrograph of HUAE cells grown for 3 days on mPTFE not precoated with Fibronectin.

For HUAE cells the cell attachment, cellular morphology and growth on TCP that had been coated with Fn was better than on uncoated TCP (Table 2). Similarly, Fn-coating of mPTFE enhanced the attachment of HUAE cells as evident after 24 hr (Table 2). This had the effect that the Fn-coated mPTFE and Fn-coated TCP surfaces supported approximately twice the number of attached cells than that seen on the uncoated surfaces. The Fn-coated mPTFE displayed a similar capacity as Fn-coated TCP for HUAE cell attachment, whilst the Fn-coated PTFE supported approximately 80% of that cell number. The morphology of the cells after 24 hr culture on Fn-coated mPTFE was markedly more spread than the cells on the mPTFE which had not been precoated with Fn, and was generally similar to the morphology of cells cultured on Fn-coated TCP. During growth over the subsequent 72 hr, the Fn-coated mPTFE maintained parity with the control Fn-coated TCP at close to confluence (See FIG. 4 and for cellular morphology, compare FIG. 6a with FIG. 6c). However, the Fn-coated PTFE sample, although maintaining good cellular morphology (FIG. 6b), exhibited a reduction in cell numbers, dropping from 75% of that of the Fn-coated TCP to only 50% after 5 days. This showed the Fn-coated PTFE surface to be only marginally better than mPTFE that had not been coated with Fn (FIG. 4 and FIG. 6d). Both the Fn-coated mPTFE and the Fn-coated TCP continued to increase in cell number at comparable rates of growth during 5 days.

The present invention is centred on the evaluation and design of materials which provide a suitable support for endothelial cells. The endothelial cells should provide an antithrombogenic surface as they do in vivo. By successfully growing endothelial cells, derived from either ovine carotid artery and human umbilical artery, on the surface of modified PTFE film and modified PTFE tubes, we have shown that the modified PTFE surface has good cell supportive characteristics. The results indicate that this chemical method of modification of PTFE may be used to improve the cell adhesive characteristics of PTFE, and this chemically modified PTFE surface would be superior to unmodified PTFE for use in implantable materials including vascular prostheses and percutaneous implants.

It will be obvious to those skilled in the art that the technique described in these Examples for enhancing the cell supportive characteristics of PTFE is applicable to expanded PTFE (sold under the registered trade mark GORE-TEX) and other fluorocarbon polymers.

The foregoing describes only some of the embodiments of the present invention and modifications, obvious to those skilled in the art, can be made thereto without departing from the scope and ambit of the invention.

We claim:

1. A process for preparing a surface for the attachment and growth of cells, said process comprising the steps of:

(i) grafting polyacrylic acid chains to a fluorocarbon polymer substrate so that the weight of the fluorocarbon polymer substrate increases by between 0.1% and 20%,
(ii) treating the fluorocarbon polymer surface produced by step (i) with concentrated sulphuric acid at a sufficiently high temperature and for a time to separately decarboxylate, aromatize and sulphonate an effective proportion of the grafted polyacrylic acid chains,
(iii) drying the surface produced by step (ii),
(iv) soaking the surface produced by step (iii) in a concentrated acid,
(v) neutralizing the surface produced by step (iv).

2. A process according to claim 1 further including the step of treating the neutralized surface with a component chosen from the group consisting of serum, cell attachment factors derived from serum, cell attachment factors derived from connective tissue, and tissue growth factors.

3. A process according to claim 2 wherein the cell attachment factor is selected from the group consisting of fibronectin and vitronectin.

4. A process according to claim 1 wherein the polyacrylic acid chains are grafted onto the fluorocarbon polymer substrate by gamma-irradiation grafting.

5. A process according to claim 1 wherein step (ii) is carried out at a temperature of 105° C. for 2 hours.

6. A process according to claim 1 wherein step (iii) is carried out at a temperature of 105° C. for 4 hours.

7. A process according to claim 1 wherein step (iv) is carried out by soaking in concentrated nitric acid at room temperature for 4 hours.

8. A process according to claim 1 wherein step (v) is carried out by washing with phosphate buffered saline at pH 7.4.

9. A process according to claim 1 wherein the fluorocarbon polymer substrate is selected from the group consisting of polytetrafluoroethylene, fluorinated ethylene propylene, polychlorotrifluoroethylene and polyvinylidine fluoride.

10. A process according to claim 1 wherein the polyacrylic acid chains are grafted onto the fluorocarbon polymer substrate by laser grafting means.

11. The product of the process of any one of claims 1 to 10.

12. The product of claim 11 wherein the surface contains about 1 sulphur atom per 75 carbon atoms.

13. The product of claim 11 used as a tissue implant.

14. The product of claim 12 used as a tissue implant.

15. A method of promoting cell attachment and growth on a surface, said method comprising the steps of:
(a) preparing a surface by:
(i) grafting polyacrylic acid chains to a fluorocarbon polymer substrate so that the weight of the fluorocarbon polymer substrate increases by between 0.1% and 20%,
(ii) treating the fluorocarbon polymer surface produced by step (i) with concentrated sulphuric acid at a sufficiently high temperature and for a sufficient time to separately decarboxylate, aromatize and sulphonate an effective proportion of the grafted polyacrylic acid chains,
(iii) drying the surface produced by step (ii),
(iv) soaking the surface produced by step (iii) in a concentrated acid,
(v) neutralizing the surface produced by step (iv); and
(b) exposing said surface to cells.

16. A method according to claim 15 wherein the cells to be attached and grown are selected from the group consisting of endothelial, epithelial, and mesenchymally-derived cells.

17. A surface for the attachment and growth of cells, the surface being prepared by:
(i) grafting polyacrylic acid chains to a fluorocarbon polymer substrate so that the weight of the fluorocarbon polymer substrate increases by between 0.1% and 20%,
(ii) separately decarboxylating, aromatizing, and sulphonating the grafted polyacrylic acid chains by treating the fluorocarbon polymer surface produce by step (i) with concentrated sulphuric acid;
(iii) drying the surface produced by step (ii),
(iv) soaking the surface produced by step (iii) in a concentrated acid, and
(v) neutralizing the surface produced by step (iv).

* * * * *